United States Patent [19]

Muhlemann

[11] 4,199,563
[45] Apr. 22, 1980

[54] DENTAL TREATMENT AGENTS AND THEIR MEDICINAL USE

[75] Inventor: Hans R. Mühlemann, Zurich, Switzerland

[73] Assignee: Bayer Aktiengesellschaft, Leverkusen, Fed. Rep. of Germany

[21] Appl. No.: 902,194

[22] Filed: May 2, 1978

[30] Foreign Application Priority Data

May 10, 1977 [DE] Fed. Rep. of Germany ....... 2720894
Jan. 20, 1978 [DE] Fed. Rep. of Germany ....... 2802489

[51] Int. Cl.$^2$ ............................................... A61K 7/16
[52] U.S. Cl. ....................................................... 424/49
[58] Field of Search ...................................... 424/49-58

[56] References Cited

U.S. PATENT DOCUMENTS

| | | | |
|---|---|---|---|
| 3,151,027 | 9/1964 | Cooley et al. | 424/52 |
| 3,955,942 | 5/1976 | Cordon et al. | 51/295 |
| 4,080,440 | 3/1978 | Digiulio et al. | 424/49 |
| 4,083,955 | 4/1978 | Grabonstetter et al. | 424/49 |

OTHER PUBLICATIONS

Chem. Abstr. 84: 133258w (1976); 83: 143739x (1975) 82: 80290a (1975); 74: 20080g (1971); 68: 94341r (1968).
Manly et al., J. Dent. Res. 28: 160–171 (1949).
Mercado et al., Arch. Oral Biol. 18: 629–635 (1973).
Olsson et al., Arch. Oral. Biol. 22: 461–466 (1977).

*Primary Examiner*—Shep K. Rose
*Attorney, Agent, or Firm*—Sprung, Felfe, Horn, Lynch & Kramer

[57] ABSTRACT

Agents, compositions containing said agents and methods are provided for covering and sealing denture injuries, occuring, for instance, in teeth being prepared to form cavities for the reception and adhesion of sealing agents and filling materials, the solid injury dressing being compatible with said filling material. The agents of the invention comprise an inorganic and/or organic cerium salt in aqueous and/or organic solution and application of said agents or compositions can be subsequently supplemented by treatment with a mineralizing solution.

8 Claims, No Drawings

DENTAL TREATMENT AGENTS AND THEIR MEDICINAL USE

Dentists have the problem of covering and sealing dentine injuries, prepared to form cavities for the reception and adhesion of sealing agents and filling materials so that the solid injury dressing is compatible with the filling. Numerous attempts have already been made in this respect.

Thus, it has already been disclosed that dentine can be treated with mineralizing solutions (Archs. oral. Biol. 17: 1005–1008, 1972: and J. Dent. Res. 55: Spec. Issue, D 135, Abstr. 117, 1976).

However, this process has the disadvantage that significant incorporation of more and/or reactive ions is only achieved after at least 30 minutes, which means that the process is unsuitable for clinical application.

It has also been disclosed to use those amphoteric or acid molecules which are capable of forming a bond with dentine on the one hand and with filling materials on the other hand (J. Dent. Res. 44: 895, 1965; and Br. Dent. J. 132: 133, 1972).

However, these processes have the disadvantage that either the required adhesion to the dentine injury very soon decreases because covering layers formed are only loosely superposed on the dentine surface, or that in the case of subsequent treatments with filling materials which are harmful to the pulp, as a result of inadequate imperviousness, the live pulp is not sufficiently protected.

The present invention relates to an agent for use in the treatment of hard tooth substance, which agent comprises an inorganic and/or organic cerium salt in aqueous and/or organic solution.

In a further aspect, the present invention provides a hard tooth substance treatment pack for use in the treatment of hard tooth substance, which pack comprises a first component comprising an agent according to the invention, and a second compound comprising a mineralizing solution.

In another aspect the present invention provides a pharmaceutical composition comprising as an active ingredient an agent according to the invention in the presence of one or more of a preservative or antiseptic agent, a flavouring agent, a surface active agent, a sweetener, a thickener, an abrasive agent, a colouring agent and a filler.

It has now been found that cut dentine can be provided with a compact, strongly adhering, impermeable surface layer or can be restructured and can thus be prepared for sealing and receiving organic filling materials, for example of the Bowen composite type or of the polyacrylic acid type and the like, by applying solutions of cerium salts to the dentine injury.

A particularly impervious surface is obtained if mineralizing solutions are additionally applied after the treatment with solutions of cerium salts.

Cerium salts are inorganic or organic salts of trivalent and quadrivalent cerium, for example $CeCl_3$, $Ce(OOCCH_3)_3$, $Ce(SO_4)_2$, cerium acetylacetone, $Ce(NH_4)SO_4$ and $Ce(NO_3)_4$ and the like. Aqueous or organic solutions, e.g. solutions in propyleneglycol, polyethyleneglycol and the like, should preferably be of from 0.1 to 30% strength, for example, from 1 to 20% strength (wgt/vol). 6% strength aqueous solutions, when used alone, or cerous chloride with pH-values of 4.0 to 5.0 and 6% strength aqueous solutions of cerous acetate with pH-values of 5.0 to 8.0 are preferred. Viscosity increasing mucilasos, e.g. hydroxyethylcellulose, carboxymethylcellulose and the like may be added.

When the cerium salt treatment of dentine is combined with subsequently applied mineralizing solutions mentioned below, solutions of cerium salts up to the saturation concentration can be used.

Various types of mineralizing solutions can be used:
1. Calcifying solutions, that is to say solutions which contain e.g. 1–4 millimols of $CaHPO_4.2H_2O$ [brushite], $Ca_3(PO_4)_2$ or $Ca(OH)_2$ per liter, with pH values of from 6.0–8.0.
2. Fluoride solutions, for example $NaF$, $NH_4F$, $SrF_2$, $FeF_3$, $SnF_2$ [Fluoristan] and amine fluorides [e.g. Olaflur, Hetaflur].
3. Solutions containing fluoride ions and phosphate ions ("Acidulated Phosphate Fluoride", APF), with a fluoride ion content of up to 2%.
4. Sodium monofluorophosphate ($Na_2PO_3F$), MFP.

The cerium solutions and mineralizing solutions may be successively applied to the dentine injury with the aid of a brush or a cotton pad or swab. The action time is usually from 1 to 5 minutes.

Compared with the known processes initially mentioned, the process according to the invention has the great advantage that a solid, impermeable hard tooth substance surface is obtained by restructuring. This advantageous effect usually occurs already within from 1 to 5 minutes.

The process according to the invention can be used for sealing exposed regions of the neck of a tooth or exposed dentine from erosion and wedge-shaped defects.

The superiority of the dentine injury treatment by the process according to the invention compared with the known processes can be seen from the following experiments:

Experiment 1

Sealing of dentine injuries in human teeth by a cerous chlorine treatment.

Two cylindrical cavities, as far as possible of the same size, were each made down to the dentine in extracted molars, (which had been stored in 0.1% strength thymol) using diamond cutters and fissure burs. After cleaning with $H_2O_2$, pH 7, for 2 minutes, washing out with a water spray and drying, each cavity was treated with 6% aqueous $CeCl_3$, pH 4.5–4.9, for 2 minutes and then dried directly with air. Thereafter, the teeth were again rinsed under running water and again dried with air.

For the dyestuff permeation experiment, the cavities were filled with 5% strength methylene blue and the teeth were centrifuged for 8 minutes at 2,800 revolutions per minute in order to force the dyestuff through the dentine channels towards the pulp by means of the centrifugal force. The teeth were halved through the centres of the test cavities and control cavities, using a grinder, and were then photographed. The pictures of the ground surfaces were enlarged 68 times by a standardised projection process and the extent of the penetration of the methylene blue (MB) into the dentine under the test cavity and control cavity was measured planimetrically in $mm^2$. For 8 teeth and 16 measured halves of teeth, the average dyestuff penetration in the case of the cavities treated with 6% strength $CeCl_3$ was 1,64 $mm^2$ (MB test: MBT), and in the case of the control cavities was 7,79 mm² (MB control: MBC). The quotient MBT:MBC was thus 0.21.

Experiment II

Comparison of the sealing of dentine injuries in human teeth by six different processes.

Two cavities were again made per tooth according to the procedure in Experiment 1. One dentine cavity in each case was treated, using six different processes, whilst the second cavity served as an untreated control.

In the ultrasonic bath used for washing the teeth with ultrasound, the energy released warmed 2 liters of water from 20° C. to 28.8° C. in the course of 30 minutes at an air temperature of 25° C. In detail, the following processes were used:

Process 1: Calciumchloride: 2 minutes with 10% strength $H_2O_2$, pH 7, rinse with $H_2O$, dry with air, 2 minutes with 4.05% strength $CaCl_2$, pH 4.5, dry with air, rinse with $H_2O$, dry with air.

Process 2: Cerouschloride and after treatment with a mineralizing solution: 2 minutes with 10% strength $H_2O_2$, pH 7, rinse with $H_2O$, dry with air, 2 minutes with 6% strength $CeCl_3$, pH 4.9, dry with air, 4 minutes with a mineralizing solution (0.5 M $Na_2HPO_4$ with 2,000 pp, of $F^-$ in the form of NaF), dry with air, rinse with $H_2O$, dry with air.

Process 3: (Mineralizing solution alone): 2 minutes with 10% strength $H_2O_2$, pH 7, rinse with $H_2O$, dry with air, 4 minutes with a mineralizing solution (0,5 M $Na_2HPO_4$ with 2,000 ppm of $F^-$ in the form of NaF), dry with air, rinse with $H_2O$, dry with air.

Process 4: (Cerouschloride and ultrasonic washing in a water bath): 2 minutes with 10% strength $H_2O_2$, pH 7, rinse with $H_2O$, dry with air, 2 minutes with 6% strength $CeCl_3$, pH 4.9, dry with air, rinse with $H_2O$, dry with air, 5 minutes in an ultrasonic bath, rinse with $H_2O$, dry with air.

Process 5: (cavity lacquer): 2 minutes with 10% strength $H_2O_2$, pH 7, rinse with $H_2O$, dry with air, coating with a cavity lacquer of polystyrene, calcium fluorophosphate, calcium hydroxide, zinc oxide and di-iodide-dithymol, dry with air, rinse with $H_2O$, dry with air.

Process 6: (cavity lacquer and ultrasonic washing in a water bath): 2 minutes with 10% strength $H_2O_2$, pH 7, rinse with $H_2O$, dry with air, coating with a cavity lacquer consisting of polystyrene, calcium fluorophosphate, calcium hydroxide, zinc oxide and di-iodide-dithymol, dry with air, rinse with $H_2O$, dry with air, 5 minutes in an ultrasonic bath, rinse with $H_2O$, dry with air.

The results of the sealing of the dentine injuries by these six processes are summarised in the table which follows, in which the methylene blue permeation into the dentine, expressed in average values in mm² (planimetry) for the test (MBT) and the control (MBC) and as the quotient Q (MBT:MBC) are indicated.

| Process | Number of teeth | Test process mm² | Control mm² | Q |
|---|---|---|---|---|
| 1 | 5 | 7816 | 8220 | 0.95 |
| 2 | 10 | 944 | 12010 | 0.08 |
| 3 | 5 | 4815 | 4855 | 0.99 |
| 4 | 8 | 1135 | 10050 | 0.11 |
| 5 | 4 | 8359 | 9556 | 0.88 |
| 6 | 8 | 9728 | 12339 | 0.79 |

It can thus be seen that quotients Q are obtained by the processes 2 and 4 according to the invention which are far superior to those which are obtained by the known processes. This applies, above all, when a treatment with mineralizing solutions is carried out subsequent to the cerium treatment.

Experiment III

In order to further demonstrate the micromorphological changes in dentine induced by treatment with cerium solutions, thin sections of dentine from human teeth were treated on one side by the six processes described in Experiment II and then analysed optoelectronically.

If the boundary area between the untreated dentine (control) and the dentine treated according to process 2 (test) are viewed when enlarged 1,950 times, a sharply defined, sealed covering layer which is resistant to washing is found on the test side and is lacking on the control side.

The treatment of the dentine injury with solutions of cerium salts thus leads not only to better sealing but also to better adhesion of this injury dressing.

Artificial and natural dentine injuries, for example in regions of the neck of a tooth, which are treated by the process according to the invention are more impervious, more resistant to acids and to harmful influences of filling materials or chemical irritation caused by food than the untreated tooth. For these reasons, dentine injuries sealed according to the invention provide favourable conditions for further dental measures, for example sealing of dentine, filling therapy using the most diverse materials, which irritate the pulp, cements which are tolerated by the pulp, local treatment of over-sensitivity of exposed necks of teeth, wedge-shaped cervical defects and advanced erosions. The agents according to the invention are also suitable for self-treatment with cerium-containing dabbing solutions, jellies or toothpastes for influencing painful necks of teeth.

EXAMPLE 1

A recent dentine injury which has been cleaned beforehand with hydrogen peroxide is coated with a freshly prepared aqueous 6% strength cerous chloride solution for 4 minutes with the aid of a brush. The dentine is then dried with air. An impermeable layer which is resistant to ultrasonic waves and can be detected as in Experiments I and II is obtained on the dentine.

Instead of the cerium chloride solution mentioned, it is also possible to use other solutions of cerium salts, for example a 6% strength cerium acetate solution.

EXAMPLE 2

A recent dentine injury which has been treated, according to Example 1, with a 6% strength cerous chloride solution is then coated with a 0.5 molar $KH_2PO_4$ solution, which has been saturated with $Ca(H_2PO_4)_2$, for three minutes with the aid of a cotton pad. After rinsing, a thick, impervious precipitate layer which can be detected as in Experiments II and III is obtained.

EXAMPLE 3

A wedge-shaped defect in the neck of a tooth in the region of the root cement is cleaned with hydrogen peroxide and sodium hypochlorite and dabbed with a freshly prepared aqueous 6% strength solution of cerous chloride for three minutes.

A 0.5 molar Na₂HPO₄ solution, which contains 2,000 ppm of fluoride ions in the form of sodium fluoride, is then brushed on. After rinsing, there is a solid layer on the treated area, which is resistant to acid, adheres well and can be detected as in Experiments II and III.

EXAMPLE 4

Solution for dabbing painful necks of teeth

| | |
|---|---|
| Cerous Chloride | 10.0 |
| Hydroxyethylcellulose | 1.0 |
| Aromatic agents | 0.1 |
| Aqua destillata | to 100.0 |

EXAMPLE 5

Solution for dabbing painful dentine exposed by cavity preparation

| | |
|---|---|
| Cerous chloride | 6.0 |
| Propyleneglycol | 2.0 |
| Polyethyleneglycol | 4.5 |
| Carboxymethylcellulose | 1.0 |
| Methylene chloride | 10.0 |
| Aqua destillata | to 100.0 |

EXAMPLE 6

Toothpaste

| | |
|---|---|
| Cerous chloride | 5.0 |
| Cerous fluoride | 0.1 |
| Cerous oxide | 5.0 |
| Aerosil 200 | 30.0 |
| Hydrated aluminium oxide | 10.0 |
| Quartz powder | 10.0 |
| Glycerol | 5.0 |
| Titanium oxide | 1.0 |
| Sodium benzoate | 0.5 |
| Lauryl sulphate | 1.0 |
| Carboxymethylcellulose | 2.0 |
| 70 % strength sorbitol solution | to 100.0 |

What is claimed is:

1. In a process for covering and sealing a dentine injury, the improvement which comprises the one-step process of contacting the exposed regions of a tooth having said dentine injury with an effective amount of a cerium salt selected from the group consisting of $CeCl_3$, $Ce(OOCCH)_3$, $Ce(SO_4)_2$, cerium acetylacetone, $Ce(NH_4)SO_4$ and $Ce(NO_2)_4$ and mixtures thereof in a solution strength between 0.1 and 30% wt./vol. dabbing solution, jelly or toothpaste.

2. The process of claim 1 wherein the cerium salt is present in a solution strength of 1 to 20%.

3. The process of claim 1 wherein the process is effected in the form of a dabbing solution.

4. The process of claim 1 wherein the process is effected in the form of a jelly.

5. The process of claim 1 wherein the process is effected in the form of a toothpaste.

6. The process of claim 2 wherein the process is effected in the form of a dabbing solution.

7. The process of claim 2 wherein the process is effected in the form of a jelly.

8. The process of claim 2 wherein the process is effected in the form of a toothpaste.